(12) United States Patent
Moinard et al.

(10) Patent No.: US 11,504,940 B2
(45) Date of Patent: Nov. 22, 2022

(54) LAMINATED ASSEMBLY AND MANUFACTURING METHOD

(71) Applicant: APLIX, Le Cellier (FR)

(72) Inventors: Nathalie Moinard, Le Cellier (FR); Thierry Marche, Le Cellier (FR)

(73) Assignee: APLIX, Le Cellier (FR)

( * ) Notice: Subject to any disclaimer, the term of this patent is extended or adjusted under 35 U.S.C. 154(b) by 259 days.

(21) Appl. No.: 16/316,653

(22) PCT Filed: Jul. 11, 2017

(86) PCT No.: PCT/FR2017/051899
§ 371 (c)(1),
(2) Date: Jan. 10, 2019

(87) PCT Pub. No.: WO2018/011516
PCT Pub. Date: Jan. 18, 2018

(65) Prior Publication Data
US 2019/0248104 A1   Aug. 15, 2019

(30) Foreign Application Priority Data

Jul. 15, 2016 (FR) ...................................... 1656808

(51) Int. Cl.
*B32B 5/02* (2006.01)
*B32B 7/14* (2006.01)
(Continued)

(52) U.S. Cl.
CPC ........ *B32B 5/022* (2013.01); *A61F 13/15699* (2013.01); *B32B 5/26* (2013.01);
(Continued)

(58) Field of Classification Search
USPC ............... 442/181, 183, 327, 370, 381, 394; 156/163, 291
See application file for complete search history.

(56) References Cited

U.S. PATENT DOCUMENTS 6,114,263 A    9/2000 Benson et al.
6,383,431 B1   5/2002 Dobrin et al.
(Continued)

FOREIGN PATENT DOCUMENTS

CN    1610531 A    4/2005
CN    1950555 A    4/2007
(Continued)

OTHER PUBLICATIONS

International Search Report and Written Opinion dated Aug. 28, 2017, in corresponding International Application No. PCT/FR2017/051899 (12 pages).
(Continued)

*Primary Examiner* — Lynda Salvatore
(74) *Attorney, Agent, or Firm* — Bookoff McAndrews, PLLC

(57) ABSTRACT

A laminated assembly extends in a longitudinal direction and a lateral direction orthogonal to the longitudinal direction, the assembly including a non-woven sheet and an elastic film that are laminated together, the non-woven sheet including at least one activated zone extending over the length of the non-woven sheet measured in the longitudinal direction and over a width that is strictly less than the width of the non-woven sheet measured in the lateral direction, the degree of activation of the activated zone of the non-woven sheet in the lateral direction being different from the degree of activation of the elastic film in the lateral direction, the degree of activation of the activated zone of the non-woven sheet in the lateral direction lying in the range 20% to 200%.

23 Claims, 6 Drawing Sheets

(51) Int. Cl.
  *B32B 27/12* (2006.01)
  *B32B 27/30* (2006.01)
  *B32B 27/32* (2006.01)
  *B32B 5/26* (2006.01)
  *A61F 13/15* (2006.01)
  *B32B 7/05* (2019.01)
  *B32B 37/12* (2006.01)
  *B32B 37/18* (2006.01)
  *B32B 38/00* (2006.01)

(52) U.S. Cl.
  CPC ............... *B32B 7/05* (2019.01); *B32B 7/14* (2013.01); *B32B 27/12* (2013.01); *B32B 27/302* (2013.01); *B32B 27/32* (2013.01); *B32B 27/327* (2013.01); *B32B 37/1292* (2013.01); *B32B 37/182* (2013.01); *B32B 38/0012* (2013.01); *B32B 2038/0028* (2013.01); *B32B 2262/0253* (2013.01); *B32B 2307/51* (2013.01); *B32B 2307/516* (2013.01); *B32B 2307/54* (2013.01); *B32B 2555/00* (2013.01); *B32B 2555/02* (2013.01)

(56) References Cited

U.S. PATENT DOCUMENTS

| | | | |
|---|---|---|---|
| 2004/0135286 A1* | 7/2004 | Ying | B29C 55/18 264/235.8 |
| 2006/0135024 A1* | 6/2006 | Thomas | B32B 5/022 442/394 |
| 2006/0148354 A1 | 7/2006 | Shelley et al. | |
| 2007/0141303 A1* | 6/2007 | Steindorf | B32B 25/10 428/136 |
| 2011/0151739 A1* | 6/2011 | Bosler | A61F 13/4902 442/396 |

FOREIGN PATENT DOCUMENTS

| | | |
|---|---|---|
| CN | 101534777 A | 9/2009 |
| DE | 29825018 U1 | 4/2004 |
| EP | 0803602 A1 | 10/1997 |
| EP | 2799606 A1 | 11/2014 |
| EP | 3316834 B1 | 10/2021 |
| JP | 2009-536888 A | 10/2009 |
| JP | 2015-529165 A | 10/2015 |
| WO | WO 94/20298 A1 | 9/1994 |
| WO | WO 03/007864 A1 | 1/2003 |
| WO | 2005/065947 A1 | 7/2005 |
| WO | 2005/110748 A1 | 11/2005 |
| WO | 2006/073975 A1 | 7/2006 |
| WO | 2007/061486 A1 | 5/2007 |
| WO | 2014/159724 A1 | 10/2014 |

OTHER PUBLICATIONS

Chinese Office Action issued in Patent Application No. 201780044241.8, dated Jul. 22, 2020, with English translation (13 pages).
Official Communication issued in Japanese Patent Application No. 2019-501559, dated May 25, 2021 (9 pages).
Office Action issued in Chinese Patent Application No. 201780044241.8, dated Mar. 22, 2021 (28 pages).
Supplementary Search Report issued in Chinese Patent Application No. 201780044241.8, dated Mar. 11, 2021 (2 pages).
Kuraray, Septon and Hybrar, Product Information, Accessed Apr. 5, 2022, <www.kurary.com/products/septon>, (12 pages).

* cited by examiner

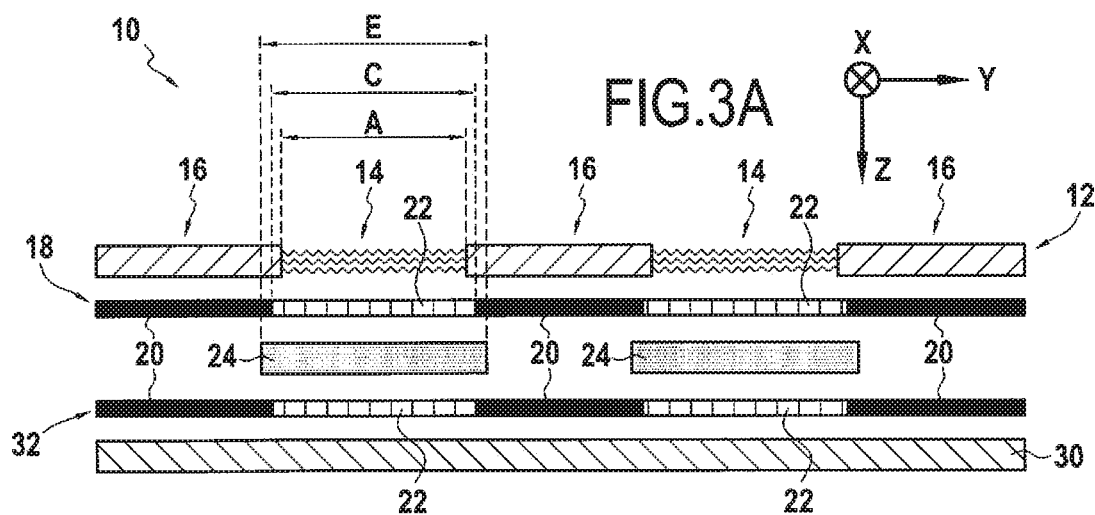
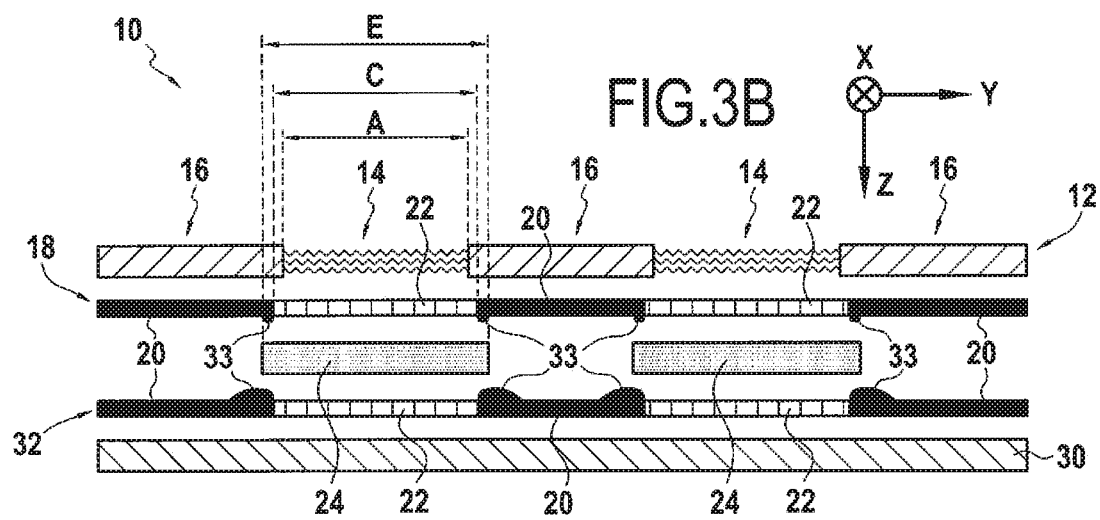
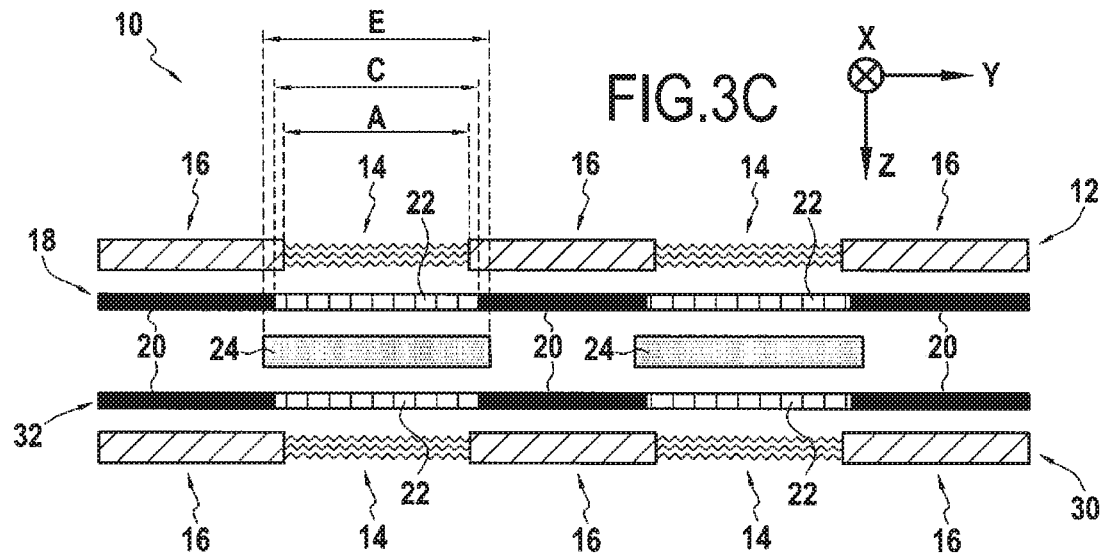

LAMINATED ASSEMBLY AND MANUFACTURING METHOD

CROSS-REFERENCE TO RELATED APPLICATIONS

This application is the U.S. national phase entry under 35 U.S.C. § 371 of International Application No. PCT/FR2017/051899, filed on Jul. 11, 2017, which claims priority to French Patent Application No. 1656808, filed on Jul. 15, 2016.

BACKGROUND OF THE INVENTION

The present disclosure relates to laminated assemblies comprising non-woven sheets.

More particularly, the present disclosure relates to non-woven sheets and to laminated assemblies suitable for use in the field of hygiene, in particular for fabricating the elastic tabs of disposable diapers.

In general, such laminated assemblies comprise two non-woven sheets secured to an elastic film that is interposed between the two non-woven sheets, the two non-woven sheets and the elastic film being assembled together by lamination in order to form a laminated assembly, also referred to as a trilaminate.

Such non-woven sheets generally present elongation capacity that is less than the elongation capacity of the elastic film, such that it is difficult to obtain easily a product with a desired elongation capacity. It is then necessary to perform treatment on the trilaminate in order to stretch it transversely so as to give it the desired transverse elongation capacity.

Nevertheless, while fabricating such a laminated assembly, during that treatment, certain defects may appear such as holes in the laminated assembly, and more particularly in the elastic film, which may lead to the laminated assembly breaking on the fabrication line or when it is pulled in the elongation direction, or indeed to undesired pollution of the laminated assembly, leading to the production line being stopped in order to clean it. Furthermore, when the laminated assembly includes holes, cuts, or splits, or is polluted it cannot be used and it is scrapped. While the laminated assembly is in the non-stretched state some holes are visible to the naked eye and they may become larger when the laminate is stretched. They are therefore easy to detect. In contrast other holes may be present in the elastic only and may be visible to the naked eye only once the laminated assembly is in the stretched state. They are then difficult to detect. Other holes, cuts, or splits may also form firstly during the above-described treatment and/or secondly on the first occasion the laminated assembly is extended, e.g. when the laminate is used on the finished product, such as a disposable diaper, causing it to break. These holes, cuts, and/or splits are then very difficult to detect since they are detected on the final application. Under all circumstances, such holes degrade the quality of the finished product as perceived by the user. Splits in the elastic film are particularly difficult to detect when they extend in the longitudinal direction, and they may form in particular during the above-described treatment because of the large amount of transverse stretching used for giving the trilaminate the desired capacity for transverse elongation and/or in particular because of the presence of hard points included in the elastic film.

OBJECT AND SUMMARY OF THE INVENTION

The present disclosure seeks to remedy those drawbacks, at least in part.

To this end, the present disclosure provides a laminated assembly extending in a longitudinal direction and a lateral direction orthogonal to the longitudinal direction, the assembly comprising a non-woven sheet and an elastic film that are laminated together, the non-woven sheet including at least one activated zone extending over the length of the non-woven sheet measured in the longitudinal direction and over a width that is strictly less than the width of the non-woven sheet measured in the lateral direction, the degree of activation of the activated zone of the non-woven sheet in the lateral direction being different from the degree of activation of the elastic film in the lateral direction, the degree of activation of the activated zone of the non-woven sheet in the lateral direction lying in the range 20% to 200%.

Since the non-woven sheet and the elastic film present different degrees of activation, it is understood that the non-woven sheet is activated before being laminated with the elastic film.

Because of this activation of the non-woven sheet before being assembled with the elastic film, a laminated assembly is obtained that presents good elongation capacity in the lateral direction, and it becomes possible to reduce or even to eliminate activation of the laminated assembly, i.e. to reduce the degree to which the laminated assembly is activated, with it even being possible for the laminated assembly to be subjected to a degree of activation that is equal to zero (no activation of the laminated assembly).

In the present disclosure, the term "non-woven" covers all non-woven fabrics coming within the definition commonly used by the person skilled in the art, typically being a sheet comprising fibers and/or filaments that are consolidated.

The term "elastic film" is used to mean a film that may be stretched without breaking under the effect of a stretching force exerted in the lateral direction and being capable of returning substantially to its initial shape and dimensions after the stretching force has been released. By way of example, it may be a film that conserves residual deformation or remanence after elongation and release (where such residual deformation is also referred to as a "permanent set" or "set") of less than 20%, more preferably less than 5%, of its initial size (before being elongated) after being elongated by 100% of its initial size, at ambient temperature (23° C.)

The term "activation" is used to mean any process during which the laminated assembly passes through an activation module that stretches the laminated assembly in a direction perpendicular to the travel direction of the laminated assembly through the activation module in order to increase the elongation capacity of the non-woven sheets of the laminated assembly.

Activating the laminated assembly comprises treatment that serves to reduce the cohesion of the structure of the non-woven sheet and to ensure that the laminated assembly may be stretched easily (with little force, e.g. 10 newtons (N)).

The inventors have identified that one of the sources of defects and/or pollution and/or the formation of holes, cuts, and/or splits lies in the laminated assembly passing through the activation module while using high degrees of activation, e.g. greater than 200%.

The inventors have thus identified that by reducing or indeed eliminating activation of the laminated assembly, the defects and/or pollution and/or holes in the laminated assembly associated with passing the laminated assembly through the activation module are reduced or even eliminated.

Specifically, the activation module comprises two activation rollers, each comprising a stack of parallel disks that are spaced apart from one another. The activation rollers and the disks have respective axes of symmetry extending in the lateral direction. The disks of the first activation roller are arranged in the gaps between the disks of the second activation roller (preferably in the middles of the gaps between the disks), and the axes of symmetry of the two activation rollers are spaced apart from each other by a distance that is less than the diameter of the disks, so that the zones of the laminated assembly that pass between the disks of the rollers are stretched in the lateral direction, thereby forming the activated zones. At those locations, the fibers and/or the filaments of the non-woven sheet are stretched and/or broken, and the elastic film is stretched. It may be understood that the smaller the distance between the axes of symmetry of two activation rollers, the greater the interpenetration of the disks of the first roller relative to the second roller, and thus the greater the degree of activation.

The degree of activation is the ratio of the difference between the distance between the ends of two adjacent disks, each belonging to a different activation roller, and the distance between the ends of the same two disks when projected onto the axis of symmetry of an activation roller divided by that distance between the ends of those same two disks projected onto the axis of symmetry of an activation roller, and it is expressed as a percentage.

When the degree of activation is large, the stretching of the laminated assembly is large and there is an increase in the risk of forming holes, cuts, or splits in the laminated assembly and in particular in the elastic film.

Furthermore, when the non-woven sheet is adhesively bonded to the elastic film, the forces exerted on the laminated assembly while passing through the activation module increase, and the disks penetrate to a greater extent into the laminated assembly, the disks possibly coming into contact with the adhesive bonding together the non-woven sheet and the elastic film. Thus, since the activation disk(s) may come into contact with the adhesive, the laminated assembly may remain bonded to the activation disk(s), and given the speed of the line, the product takes a few seconds to accumulate in the activation block, and the fabrication line needs to be stopped urgently, with there being a risk of breaking one or more activation disks. Such breakage requires lengthy and expensive maintenance action. Even if there is no breakage, it remains necessary to clean the activation module and then to restart the fabrication line. The activation disks are at even greater risk of being contaminated by the adhesive when the laminated assemblies present a non-woven sheet of low weight. In certain circumstances, the adhesive may become deposited on the laminated assembly and may pollute it. The adhesive may also tear fibers from the non-woven sheet, which may then become deposited on the laminated assembly and pollute it. Furthermore, with fibers being torn away, an undesired hole may form in the non-woven sheet.

Since the non-woven sheet is already activated, once the non-woven sheet has been laminated with the elastic film, the laminated assembly presents satisfactory elongation capacity, and the laminated assembly need not be activated. The elastic film is therefore not activated. This advantageously avoids risks of contamination associated with adhesive being transferred onto the disks of the activation module, which may lead in particular to an emergency stop of the fabrication line, avoids the elastic film being stretched, and avoids holes, cuts, and/or splits being formed in the elastic film. It is thus possible to reduce the amount of laminated assembly that is scrapped and also to reduce the length of time the production line is stopped in order to be cleaned.

It is also possible to envisage that the activated zone of the non-woven sheet is of a width that is not less than the width of the elastic film.

In order to avoid problems of delamination while activating the laminated assembly, the width of the activation zone of the laminated assembly is less than the width of the elastic film.

Since the non-woven sheet is activated prior to being assembled with the elastic film, it is possible to activate the non-woven sheet over a width that may be equal to or greater than the width of the elastic film. It may naturally be understood that the width of the activated zone could be less than the width of the elastic film.

The degree of activation of the activated zone of the non-woven sheet in the lateral direction may lie in the range 40% to 200%, and more particularly in the range 40% to 160%.

Furthermore, it is also possible for a laminated assembly that includes a non-woven sheet that was activated prior to being assembled with the elastic film, itself to be activated. Nevertheless, for identical elongation capacity of the laminated assembly since the non-woven sheet was activated before being assembled with the elastic film, the degree of activation of the laminated assembly may be activated to a degree that is less than would have been necessary if the non-woven sheet had not been activated before being assembled with the elastic film. This advantageously reduces any risk of contamination associated with adhesive being transferred onto the disks of the activation module, requiring in particular an emergency stop of the fabrication line, and stretching of the elastic film is reduced as is the risk of forming holes, cuts, and/or splits in the elastic film. The amount of adhesive that is transferred to the disks increases when using non-woven sheets that are of low weight. It is thus possible to reduce the amount of laminated assembly that is scrapped and also to reduce the length of time the production line is stopped for cleaning.

By way of example, the laminated assembly may be activated to less than 200% in the lateral direction, preferably to less than 150%, still more preferably to less than 125%, in particular to less than 100%.

The elastic film may present a width that is less than the width of the non-woven sheet.

The elastic film may be co-extruded with a non-elastic material in order to form a film of width that is substantially equal to the width of the non-woven sheet, the elastic film being assembled to the activated zone of the non-woven sheet.

The elastic film may be formed by an elastic adhesive.

The elastic film may then be extruded onto the non-woven sheet and subsequently laminated with the non-woven sheet. The activated zone may extend over the entire length of the non-woven sheet measured in the longitudinal direction.

By way of example, the non-woven sheet may be constituted by a sheet of fibers and/or filaments obtained by the dry-laid technique (dry process), the wet-laid technique (wet process), or the spun-laid technique (melt spinning/extrusion process), the fibers and/or filaments being consolidated by mechanical, thermal, chemical, and/or adhesive bonding.

The non-woven sheet may be a carded and calendared non-woven fabric.

The carded and calendared non-woven sheet is a non-woven fabric comprising a sheet of fibers presenting points of consolidation of the sheet by thermal consolidation that are distributed in substantially uniform manner over the entire sheet. Consolidation provides a degree of cohesion between the fibers enabling them to be handled and transported, and in particular enabling them to be wound in the form of a reel and subsequently unwound. Activating the carded and calendared non-woven sheet serves to lengthen and/or break the fibers of the non-woven sheet and/or to deform the consolidation points of the sheet. This increases the elongation capacity of the non-woven sheet.

The fibers of the carded and calendared non-woven sheet are lying in the range 1 deciTex (dTex) to 8 dTex, preferably in the range 1.3 dTex to 6.7 dTex, still more preferably in the range 1.6 dTex to 5.5 dTex.

Tex is the SI unit for the fineness of textile fibers. It is expressed as the weight in grams (g) for a length of 1000 meters (m) of the fibers.

The non-woven sheet may be a first non-woven sheet, the laminated assembly may include a second non-woven sheet, and the elastic film may be interposed between the first and second non-woven sheets.

With the elastic film interposed between the first and second non-woven sheets, only the non-woven sheets are accessible to the user.

The elastic film may be formed by an elastic adhesive.

The elastic adhesive may be extruded onto the first non-woven sheet and the first non-woven sheet coated in the elastic adhesive may then be laminated with the second non-woven sheet, or vice versa.

The elastic adhesive may also be extruded directly between the two non-woven sheets and subsequently the two non-woven sheets and the elastic adhesive may be laminated with one another.

The elastic film may be formed by an elastic adhesive and it may be co-extruded with a non-elastic material formed by a non-elastic adhesive in order to form a film of width that is substantially equal to the width of the non-woven sheet, the elastic film being assembled with the activated zone of the non-woven sheet.

The non-woven sheet may be a first non-woven sheet, the laminated assembly may include a second non-woven sheet, and the second non-woven sheet may be interposed at least in part between the first non-woven sheet and the elastic film.

The elastic film need not be activated.

The second non-woven sheet need not have an activated zone. The second non-woven sheet is thus not activated.

The second non-woven sheet may include at least one activated zone extending over the length of the non-woven sheet measured in the longitudinal direction and over a width that is strictly less than the width of the non-woven sheet measured in the lateral direction, and the degree of activation of the activated zone of the second non-woven sheet in the lateral direction may lie in the range 20% to 200%.

The degree of activation of the activated zone of the second non-woven sheet in the lateral direction may lie in the range 20% to 200%, in particular in the range 40% to 200%, still more particularly in the range 40% to 160%.

The degree of activation of the activated zone of the first non-woven sheet in the lateral direction may be different from the degree of activation of the activated zone of the second non-woven sheet in the lateral direction.

By separately activating the first and second non-woven sheets, it is possible, as a function of the nature of the first and second non-woven sheets, to activate each non-woven sheet to a different degree so as to adapt to the nature of each non-woven sheet so as to obtain satisfactory laminated assembly.

The degree of activation of the activated zone of the second non-woven sheet in the lateral direction may be different from the degree of activation of the elastic film in the lateral direction.

It may be understood that the laminated assembly may be activated after laminating and assembling the two non-woven sheets with the elastic film. Nevertheless, the second non-woven sheet that was activated prior to being assembled with the elastic film presents a degree of activation that is different from the degree of activation of the elastic film.

Naturally, when the laminated assembly is not activated, the degree of activation of the elastic film is zero, and the degree of activation of the second non-woven sheet is different from the degree of activation of the elastic film.

The non-woven sheet may be a non-woven sheet of Spunlace type.

A Spunlace type non-woven fabric is a non-woven fabric made from (endless) filaments and/or from fibers of a length that generally lies in the range 30 millimeters (mm) to 60 mm, that are consolidated by hydro-bonding. Spunlace type non-woven fabric is commonly used in the hygiene field because of its softness and its natural capacity for deformation. Because of its natural capacity for deformation, Spunlace non-woven fabric is particularly subject to the "neck-down" phenomenon, i.e. when tension is applied thereto in a given direction, it is subjected to a large amount of deformation in the orthogonal direction. Consequently, on a production line where it is subjected to a large amount of longitudinal tension, a Spunlace type non-woven sheet shrinks significantly in the lateral direction. Thus, for a desired width of laminated assembly, provision is generally made for a Spunlace type non-woven sheet to be of greater width in order to take account of the neck-down phenomenon.

By activating the Spunlace type non-woven sheet, it is possible, for constant laminated assembly width, to have a Spunlace type non-woven sheet that presents a width that is less than the width the Spunlace type non-woven sheet would otherwise have needed if the Spunlace type non-woven sheet had not been activated. This serves to reduce the cost of producing the laminated assembly. By prior activation of the Spunlace non-woven sheet, it is then possible to adjust its width so that it is greater than and/or equal to, or less than and/or equal to the width of the Spunlace non-woven fabric prior to passing along the fabrication line.

The non-woven sheet may be a non-woven fabric of Spunmelt type.

A Spunmelt type non-woven fabric comprises Spunbond type non-woven fabrics, Meltblown type non-woven fabrics, and non-woven fabrics comprising at least one Spunbond type layer and at least one Meltblown type layer (e.g.: SM, SMS, SSMMS, SMSMS, SMMMS, SMMS, SSMMSS, SSMMMSS, SSMMMSS, . . . or any other combination of S and M layers, where S represents a Spunbond type layer and M represents a Meltblown type layer). A Spunmelt type non-woven fabric is a non-woven fabric made from filaments obtained by extrusion.

Activating the Spunmelt type non-woven sheet serves to lengthen and/or break the filaments of the non-woven sheet. This serves to increase the elongation capacity of the non-woven sheet.

The present disclosure also provides a fabrication method for fabricating a laminated assembly extending in a longitudinal direction and in a lateral direction orthogonal to the longitudinal direction, the method comprising the following steps:

activating, in the lateral direction to a degree in the range 20% to 200%, a zone of a non-woven sheet extending over a length of the non-woven sheet measured in the longitudinal direction and over a width that is strictly less than the width of the non-woven sheet measured in the laterally direction;

providing an elastic film; and laminating the non-woven sheet with the elastic film.

The degree of activation of the activated zone of the non-woven sheet in the lateral direction may lie in the range 40% to 200%, in particular in the range 40% to 160%.

Laminating the non-woven sheet and the elastic film together serves to assemble and secure the non-woven sheet together with the elastic film. The non-woven sheet and the elastic film may be assembled and secured together with or without adhesive.

For example, it is possible to envisage encapsulating the fibers and/or the filaments of the non-woven sheet in the elastic film when the non-woven sheet is laminated with the elastic film before the film has cooled completely after being extruded.

It is also possible to envisage assembling the non-woven sheet with the elastic film by laminating the non-woven sheet or the elastic film over their entire width or by laminating over a fraction only of the width of the non-woven sheet or of the elastic film, e.g. by ultrasound welding, or by hot or cold calendaring.

Prior to laminating the non-woven sheet, the method may include a step of coating the non-woven sheet with an adhesive.

The adhesive may be deposited on the non-woven sheet in a manner that is continuous in the longitudinal direction. It may also be deposited on the non-woven sheet in a manner that is discontinuous in the longitudinal direction.

In the activated zone of the non-woven sheet, the adhesive may be deposited discontinuously in the lateral direction. In the activated zone of the non-woven sheet, the adhesive thus forms a plurality of lines of adhesive, e.g. lines that are continuous in the longitudinal direction, each of width that is less than the width of the activated zone.

It is possible to adapt the width of the lines of adhesive and their spacing across the lateral direction.

Prior to laminating the non-woven sheet, the method may include a step of coating the elastic film with an adhesive.

The non-woven sheet may be a first non-woven sheet, the fabrication method may include a step of providing a second non-woven sheet and a step of laminating the second non-woven sheet on the elastic film.

The step of laminating the second non-woven sheet on the elastic film may be performed substantially with the step of laminating the first non-woven sheet on the elastic film. These lamination steps could equally well be performed in succession.

The elastic film may be formed by an elastic adhesive.

The elastic film may be extruded onto the first non-woven sheet and the first non-woven sheet coated in the elastic adhesive may then be laminated with the second non-woven sheet, or vice versa.

The elastic adhesive may also be extruded directly between the two non-woven sheets and subsequently the two non-woven sheets and the elastic adhesive may be laminated with one another.

The non-woven sheet may be a first non-woven sheet, the fabrication method may include a step of providing a second non-woven sheet, and a step of laminating the second non-woven sheet with the first non-woven sheet. The second non-woven sheet may be laminated during lamination with the elastic or it may be laminated during a separate step, either before or after being laminated with the elastic.

Prior to laminating the second non-woven sheet, the second non-woven sheet may be activated in the lateral direction to a degree lying in the range 20% to 200% over a zone extending over the length of the non-woven sheet measured in the longitudinal direction and over a width that is strictly less than the width of the non-woven sheet measured in the lateral direction.

The degree of activation of the activated zone of the second non-woven sheet in the lateral direction may lie in the range 40% to 200%, in particular in the range 40% to 160%.

Prior to laminating the second non-woven sheet, the method may include a step of coating the second non-woven sheet with an adhesive.

The adhesive may be deposited on the non-woven sheet in a manner that is continuous in the longitudinal direction. It may also be deposited on the non-woven sheet in a manner that is discontinuous in the longitudinal direction.

In the activated zone of the non-woven sheet, the adhesive may be deposited discontinuously in the lateral direction. In the activated zone of the non-woven sheet, the adhesive thus forms a plurality of lines of adhesive, e.g. lines that are continuous in the longitudinal direction, and of width that is less than the width of the activated zone.

The laminated assembly may be activated to a degree that is less than 200% in the lateral direction, in particular less than 150%, more particularly less than 125%, still more particularly less than 100%.

BRIEF DESCRIPTION OF THE DRAWINGS

Other characteristics and advantages of the invention appear from the following description of embodiments of the invention given as non-limiting examples and with reference to the accompanying figures, in which:

FIG. 3A is exploded cross-section diagrammatic exploded view of a laminated assembly according to a third embodiment;

FIGS. 3B and 3C show variants of the third embodiment;

DETAILED DESCRIPTION OF THE INVENTION

Figure 1A:
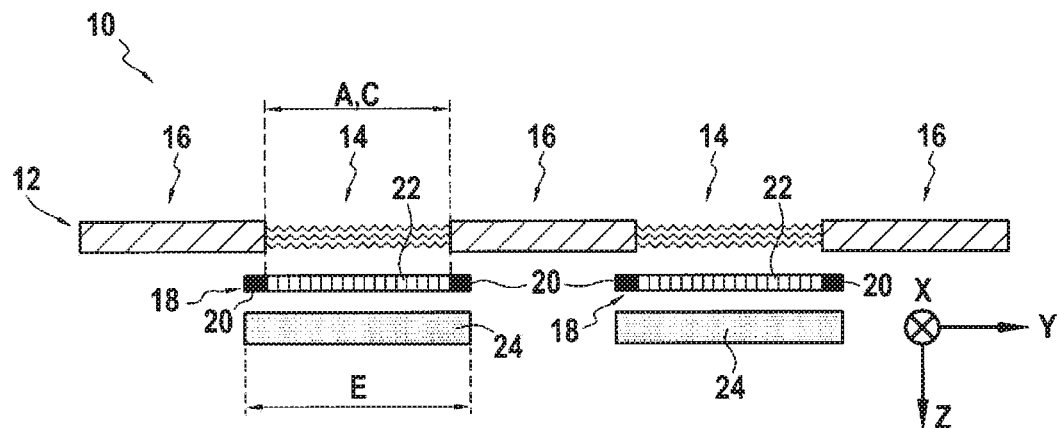
FIG. 1A is a cross-section diagrammatic exploded view of a laminated assembly according to a first embodiment.

FIG. 1A is a cross-section diagrammatic view on section plane YZ of a laminated assembly 10 according to a first embodiment. FIG. 1A is an exploded view of the assembly 10 in order to show each element of the laminated assembly 10.

This laminated assembly 10 includes a non-woven sheet 12 that extends in a longitudinal direction X and in a lateral direction Y that is orthogonal to the longitudinal direction X. Across the width of the non-woven sheet 12, the non-woven sheet 12 includes two activated zones 14 that are separated by a non-activated zone 16. The non-woven sheet 12 also has a non-activated zone 16 on each lateral margin of the non-woven sheet 12. The term "activated zones" 14 relates to a zone 14 that is activated prior to laminating. It is also referred to as a prior-activated zone 14.

By way of example, the non-woven sheet 12 may be a carded and calendared non-woven fabric, a Spunlace type non-woven fabric, or a Spunmelt type non-woven fabric.

It may be understood that the activated zones 14 are of a width that is strictly less than the width of the non-woven sheet, where width is measured in the lateral direction Y. The activated zones 14 extend along the length of the non-woven sheet 12, where length is measured in the longitudinal direction X.

The laminated assembly 10 also has two elastic films 24 that are connected to the non-woven sheet 12 by adhesive 18. The adhesive 18 is applied in solid strips 20 on the lateral margins of the elastic films 24 and in narrow lines or threads 22 on the activated zones 14 of the non-woven sheet 12.

By way of example, for the activated film 24, it is possible to envisage using elastic materials comprising a polyolefin of metallocene type, or based on styrene-isoprene-styrene block copolymers (SIS) or on poly(styrene-butadiene-styrene) (SBS). The elastic film 24 may be made up of three or more layers or it may be a skinlayer, i.e. an elastic film covered in a skin.

It should be observed that in the first embodiment of the laminated assembly 10, the width A of each activated zone 14 is less than the width E of each elastic film 24.

The difference between the width A and the width E may line in the range 8 mm to 20 mm, e.g. this difference may be 14 mm. Such a difference makes it possible to obtain a greater density of fibers and/or filaments in the non-activated zone so as to allow for better fastening between the elastic film 24 and the corresponding non-woven sheet 12. The sum of the widths of the activated zones may lie in the range 20% to 80% of the width of the corresponding non-woven sheet 12, and in particular in the range 35% to 70% of the width of the non-woven sheet 12.

Furthermore, the adhesive 18 is applied to the non-woven sheet 12 over a width that is equal to the width E of the elastic film 24. The zone where the adhesive is applied in threads presents a width C that is less than the width E of the elastic film and that is substantially equal to the width A of the activated zone 14. Thus, with the adhesive 18 arranged in solid strips 20 of the lateral margins of the elastic films 24 and the non-activated zones 16 of the non-woven sheet 12, firm fastening is ensured of the elastic films 24 on the non-woven sheet.

Nevertheless, it is possible to envisage that the width C of the zone where the adhesive is applied in threads is different from the width A of the activated zone.

In the first embodiment, the non-woven sheet 12 has two activated zones 14, however it could have only one. It could equally well have more than two.

In the first embodiment, the two activated zones 14 are of the same width A. Naturally, it is possible to envisage the two activated zones 14 having different widths.

Furthermore, the elastic films 24 are not activated. The degree of activation of the activated zones 14 of the non-woven sheet 12 is thus greater than the degree of activation of the elastic films, so they are different.

It is also possible to envisage activating the laminated assembly 10 in the zones of the laminated assembly where the elastic film 24 is present. Since the non-woven sheet 12 is activated prior to laminating the non-woven sheet 12 with the elastic film 24, i.e. prior to laminating, the degree of activation of the activated zones 14 of the non-woven sheet 12 is modified by activating the laminated assembly 10. Nevertheless, the resulting degree of activation of the activated zones 14 of the non-woven sheet in the lateral direction Y continues to remain different from the degree of activation of the elastic film 24 in the lateral direction Y, in particular the resulting degree of activation of the activated zones 14 of the non-woven sheet in the lateral direction Y is greater than the degree of activation of the elastic film 24 in the lateral direction Y.

Nevertheless, because the non-woven sheet 12 was activated prior to being laminated with the elastic films 24, in order to obtain the same elongation capacity for the laminated assembly 10, the degree of activation that is applied to the laminated assembly 10 may be less than the degree of activation that would otherwise have been necessary for the laminated assembly 10 if the non-woven sheet 12 had not been activated prior to being laminated with the elastic films 24. This serves to reduce the risk of polluting the laminated assembly 10 and/or the risk of creating holes, cuts, and/or splits in the elastic films 24.

Furthermore, it is also possible to envisage that the degree of activation in each activated zone 14 of the non-woven sheet 12 in the lateral direction Y differs from one activated zone to the other.

Figure 10:
FIG. 10 is a diagram showing the steps of a method of fabricating a laminated assembly.

With reference to FIG. 10, the non-woven sheet 12 is activated in step 200 during which the two activated zones 14 of the non-woven sheet 12 are made.

Thereafter, the adhesive 18 is deposited by being coated on the non-woven sheet 12 in step 202, and the elastic films 24 are applied to the non-woven sheet 12 coated in adhesive 18 in step 204. The non-woven sheet 12 coated in adhesive 18 and the elastic films 24 are laminated together in step 206 in order to form a laminated assembly 10. In a variant, it would be possible to envisage depositing the adhesive 18 on the elastic film 24 instead of depositing the adhesive 18 on the non-woven sheet 12.

Thereafter, the laminated assembly 10 may be subjected to activation of the laminated assembly 10 in the lateral direction Y during step 208.

Figure 1B:
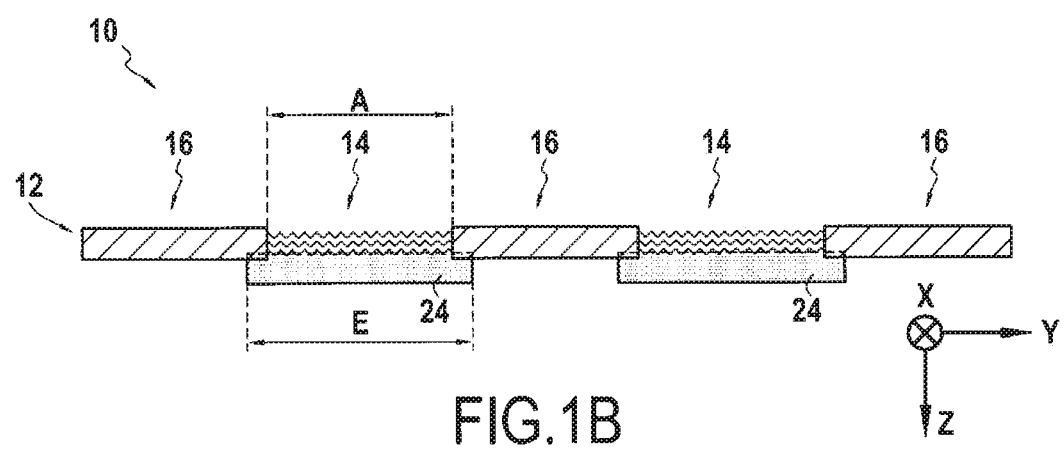
FIG. 1B shows a variant of the first embodiment.

In the variant of the first embodiment that is shown in FIG. 1B, the laminated assembly 10 does not include adhesive 18. FIG. 1B is not an exploded view of the laminated assembly 10.

In this variant, step 202 is not performed. Specifically, in this variant, the elastic film 24 is extruded and before the elastic film 24 has cooled completely, the non-woven sheet 12 is laminated with the elastic film 24 so that the fibers and/or filaments of the non-woven sheet 12 are encapsulated in the elastic film 24.

Below, elements that are common to the various different embodiments are identified by the same numerical references and they are not described in greater detail.

Figure 2:
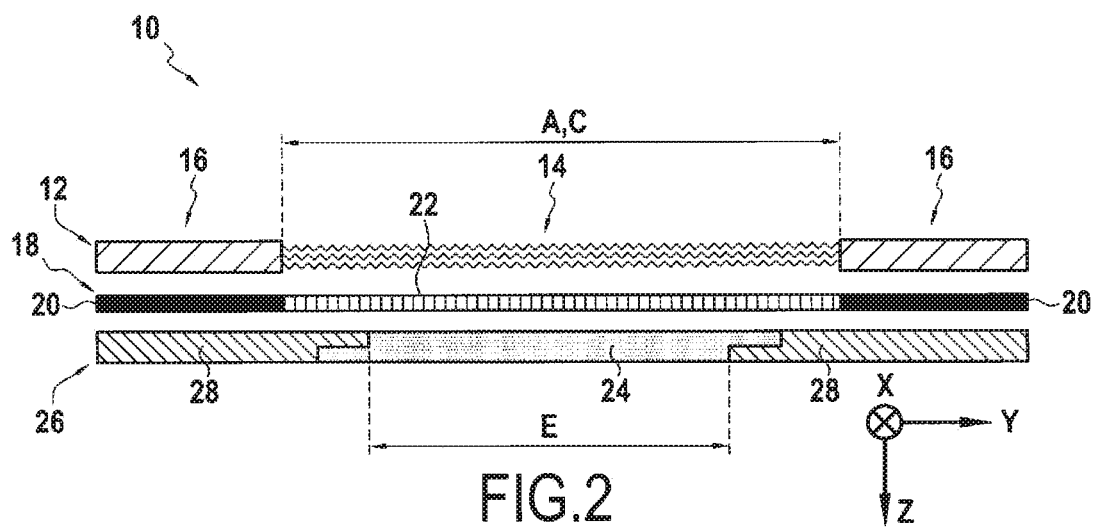
FIG. 2 is exploded cross-section diagrammatic exploded view of a laminated assembly according to a second embodiment.

In the second embodiment shown in FIG. 2, the non-woven sheet 12 of the laminated assembly 10 has an activated zone 14 arranged between two non-activated zones 16. The non-activated zones 16 are present on each laminated margin of the non-woven sheet 12.

The laminated assembly includes a film 26 comprising the elastic film 24 that has been co-extruded with a non-elastic plastics material 28, e.g. a material based on polyethylene.

In the second embodiment, the width A of the activated zone 14 is equal to the width C of the zone where adhesive is applied in threads 22, and the width E of the elastic film 24 is less than the width A of the activated zone 14. Nevertheless, the width C could be less than the width E. Thus, since the adhesive 18 is arranged in solid strips 20 on the lateral margins of the film 26, the film 26 is fastened firmly on the non-woven sheet 12.

Furthermore, the film 26 could include a plurality of elastic films 24, each elastic film being separated from the others by a non-elastic plastics material 28 co-extruded with the elastic films 24. With a plurality of elastic films 24, the non-woven sheet 12 could then include a plurality of activated zones 14 arranged in register with the elastic films 24, or the non-woven sheet 12 could have only one activated zone 14.

In the third embodiment shown in FIG. 3A, the laminated assembly 10 includes two non-woven sheets 12 and 30. The first non-woven sheet 12 is similar to the non-woven sheet 12 of FIG. 1A. The second non-woven sheet 30 does not have a zone that was activated prior to lamination. The second non-woven sheet 30 may be a spunlace type non-woven fabric.

The elastic films 24 are connected to the second non-woven sheet 30 by adhesive 32. Like the adhesive 18, the adhesive 32 is applied in solid strips 20 on the lateral margins of the elastic films 24 and in narrow lines or threads 22 on the activated zones 14 of the second non-woven sheet 30.

In the third embodiment (FIGS. 3A, 3B, and 3C), it can be observed that the width E of the elastic film 24 is greater than the width A of the activated zone 14, and that the zone where the adhesive is applied in threads presents a width C that is less than the width E of the elastic film, but greater than the width A of the activated zone 14.

As in the first embodiment, the first non-woven sheet 12 of the third embodiment includes two activated zones 14, but it could include only one. It could also include more than two.

In the third embodiment, the two activated zones 14 are of the same width A. It would naturally be possible to envisage the two activated zones 14 being of different widths.

The elastic films 24 are not activated. The degree of activation of the activated zones 14 of the first non-woven sheet 12 is thus greater than the degree of activation of the elastic films, so they are different. The second non-woven sheet 30 is not activated, such that the degree of activation of the second non-woven sheet, equal to zero, is different from the degree of activation of the activated zones 14 of the first non-woven sheet 12.

It is also possible to envisage activating the laminated assembly 10 in the zones of the laminated assembly where the elastic film 24 is present. Since the first non-woven sheet 12 was activated prior to the first non-woven sheet 12 being laminated with the elastic film 24, i.e. prior to rolling, the degree of activation of the activated zones 14 of the first non-woven sheet 12 is modified by activating the laminated assembly 10. Nevertheless, the resulting degree of activation of the activated zones 14 of the first non-woven sheet 12 in the lateral direction Y continues to remain different from the degree of activation of the elastic film 24 in the lateral direction Y. The degree of activation of the second non-woven sheet 30 is different from the degree of activation of the activated zones 14 of the first non-woven sheet 12, and in particular the resulting degree of activation of the activated zone 14 of the non-woven sheet 12 in the lateral direction Y is greater than the degree of activation of the elastic film 24 in the lateral direction Y.

With reference to FIG. 10, it can be understood that in step 202, each non-woven sheet 12, 30 is coated in adhesive 18, and in step 204, the elastic films 24 are applied between the two non-woven sheets 12, 30 prior to the two non-woven sheets 12, 30 being laminated with the elastic films 24 in order to form the laminated assembly 10 of FIG. 3A.

Nevertheless, it is also possible to envisage that in step 206, the elastic films 24 are laminated with the first non-woven sheet 12 prior to being laminated subsequently with the second non-woven sheet 30, or vice versa.

In the variant of the third embodiment that is shown in FIG. 3B, the laminated assembly 10 differs from the laminated assembly of FIG. 3A in that the adhesive 18, 32 presents extra thicknesses 33 that provide even firmer fastening of the elastic films 24 on the non-woven sheets 12, 30.

In the variant of the third embodiment shown in FIG. 3C, the laminated assembly 10 differs from the laminated assembly of FIG. 3A in that the second non-woven sheet 30 is similar to the non-woven sheet 12 of FIG. 1A.

The second non-woven sheet 30 could include more than two activated zones 14. The activated zones 14 of the first non-woven sheet 12 could present a width that is different from the activated zones 14 of the second non-woven sheet 30. Furthermore, the activated zones 14 of each non-woven sheet 12, 30 could present different widths.

Figure 4:
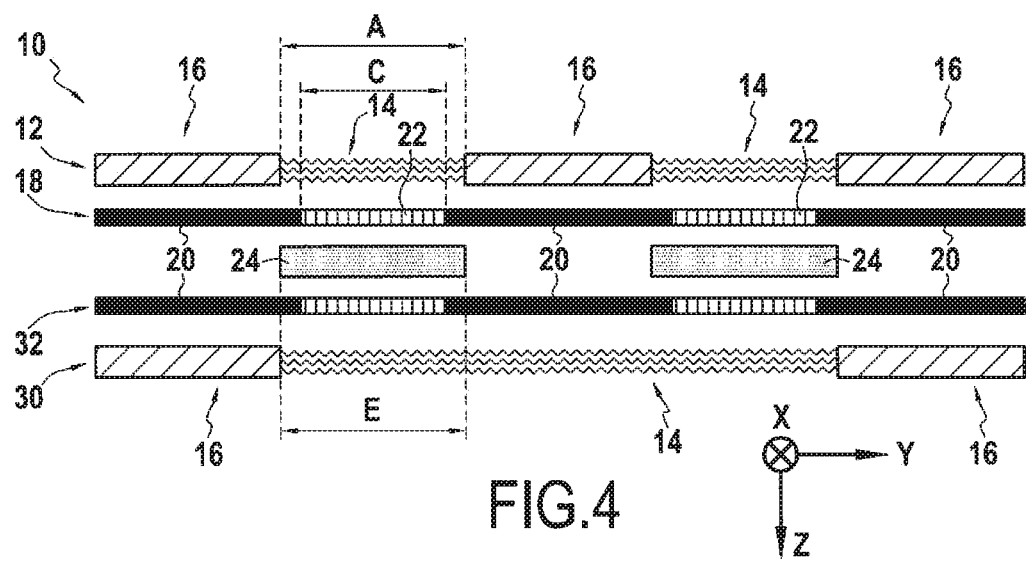
FIG. 4 is exploded cross-section diagrammatic exploded view of a laminated assembly according to a fourth embodiment.

In the fourth embodiment shown in FIG. 4, the laminated assembly 10 includes two non-woven sheets 12, 30. The first non-woven sheet 12 is similar to the non-woven sheet 12 of FIG. 1A and the second non-woven sheet 30 is similar to the non-woven sheet 12 of FIG. 2 that includes an activated zone 14.

It should be observed that in the fourth embodiment of the laminated assembly 10, the width A of each activated zone 14 of the first non-woven sheet 12 is equal to the width E of each elastic film 24.

Furthermore, the adhesive 18 is applied over the entire width of the non-woven sheet 12. The zone where the adhesive is applied in threads presents a width C that is less than the width E of the elastic film. Thus, since the adhesive 18 is arranged in solid strips 20 on the lateral margins of the elastic films 24, the elastic films 24 are fastened firmly on the non-woven sheet.

Nevertheless, it is possible to envisage that the width A of the activated zones is different from the width of the elastic films E. The width A could be less than or greater than the width E.

In the fourth embodiment, the first non-woven sheet 12 includes two activated zones 14, however it could include only one. It could equally well include more than two.

In the fourth embodiment, the two activated zones 14 of the first non-woven sheet 12 have the same width A. Naturally, it is possible to envisage the two activated zones 14 previously having different widths.

In the fourth embodiment, the second non-woven sheet 30 includes one activated zone 14, however it could include more than one.

Furthermore, the elastic films 24 are not activated. The degree of activation of the activated zones 14 in each non-woven sheet 12, 30 is thus greater than the degree of activation of the elastic films, the degrees of activation of each non-woven sheet 12, 30 in the lateral direction Y are thus different from the degree of activation of the elastic films 24 in the lateral direction Y. In addition, the degree of activation of the first non-woven sheet 12 in the lateral direction Y may be different from the degree of activation of the second non-woven sheet 30 in the lateral direction Y.

It is also possible to envisage activating the laminated assembly 10 in the zones of the laminated assembly where the elastic film 24 is present. Since the non-woven sheets 12 and 30 were activated prior to laminating the non-woven sheets 12, 30 with the elastic films 24, i.e. prior to rolling, the degree of activation of the activated zones 14 of each non-woven sheet 12, 30 is modified by activating the laminated assembly 10. Nevertheless, the resulting degree of activation of the activated zones 14 of each non-woven sheet 12, 30 in the lateral direction Y continues to remain different from the degree of activation of the elastic film 24 in the lateral direction Y, and in particular the resulting degree of activation of the activated zones 14 of each non-woven sheet 12, 30 in the lateral direction Y is greater than the degree of activation of the elastic film 24 in the lateral direction Y.

Figure 5:
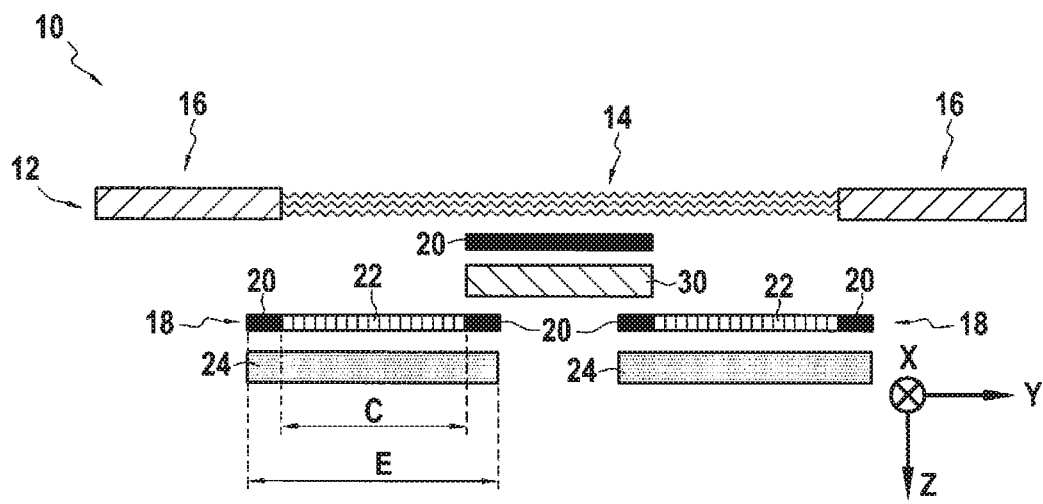
FIG. 5 is a cross-section diagrammatic exploded view of a laminated assembly according to a fifth embodiment.

In the fifth embodiment shown in FIG. 5, the laminated assembly 10 includes two non-woven sheets 12, 30. The first non-woven sheet 12 is similar to the non-woven sheet 12 of FIG. 2 and the second non-woven sheet 30 is similar to the second non-woven sheet 30 of FIG. 3A that does not include an activated zone.

In the fifth embodiment, the second non-woven sheet 30 is interposed in part between the first non-woven sheet 12 and the elastic films 24. The second non-woven sheet 30 does not have an activated zone and it is coated in a solid strip 20 of adhesive. The second non-woven sheet 30 in this fifth embodiment acts as reinforcement for the first non-woven sheet 12, in particular for the activated zones 14 of the first non-woven sheet 12.

By way of example, the second non-woven sheet 30 may be a carded calendared non-woven fabric or a Spunmelt type non-woven fabric. As shown in FIG. 5, the second non-woven sheet 30 in this example presents a width that is much less than the width of the first non-woven sheet 12.

It should be observed that the adhesive 18 is applied in solid strips 20 between the elastic films 24 and the non-woven sheets 12, 30 so that the solid strips 20 are present on the non-activated zones of the non-woven sheets 12, 30. This serves to provide firm fastening of the elastic films 24 on the non-woven sheets 12, 30.

It should be observed that between the second non-woven sheet 30 and the two elastic films 24, there is no adhesive 18 arranged between the two elastic films in the lateral direction Y.

As in the above embodiments, it is possible to envisage having different widths A, E, and D, and it is also possible to envisage having a different number of elastic films 24 and/or of activated zones 14.

It is also possible to envisage activating the laminated assembly 10 in the zones of the laminated assembly where the elastic film 24 is present. Since the first non-woven sheet 12 was activated before laminating the non-woven sheets 12, 30 with the elastic films 24, i.e. prior to rolling, the degree of activation of the activated zone 14 of the first non-woven sheet 12 is modified by activating the laminated assembly 10. Nevertheless, the resulting degree of activation of the activated zone 14 of the first non-woven sheet 12 in the lateral direction Y continues to remain different from the degree of activation of the elastic film 24 in the lateral direction Y. The second non-woven sheet 30 is not activated such that the degree of activation of the second non-woven sheet 30 in the lateral direction Y, which is equal to zero, is different from the degree of activation of the activated zone 14 of the first non-woven sheet 12, and is different from the degree of activation of the elastic film 24 in the lateral direction Y, in particular the resulting degree of activation of the activated zones 14 of the non-woven sheet 12 in the lateral direction Y is greater than the degree of activation of the elastic film 24 in the lateral direction Y.

With reference to FIG. 10, it may be understood that in step 202, the first non-woven sheet 12 or the second non-woven sheet 30 is coated in a solid strip 20 of adhesive 18 and that the elastic films 24 are also coated in adhesive 18, while in step 204, the second non-woven sheet 30 is applied against the first non-woven sheet 12 and the elastic films 24 are applied against the two non-woven sheets 12, 30 so that the second non-woven sheet 30 is interposed in part between the first non-woven sheet 12 and the elastic films 24. The two non-woven sheets 12, 30 are laminated with the elastic films 24 in order to form the laminated assembly 10 of FIG. 5.

It may be understood that the second non-woven sheet 30 is laminated with the first non-woven sheet 12. This step may be performed at the same time as the elastic films 24 are laminated with both non-woven sheets 12 and 30. These two lamination operations could equally well be performed in consecutive manner. It is also possible to apply a third non-woven sheet on which adhesive may be arranged and then to apply this third non-woven sheet to the faces of the elastic films 24 that face away from the first and second non-woven sheets 12 and 30.

Figure 6A:
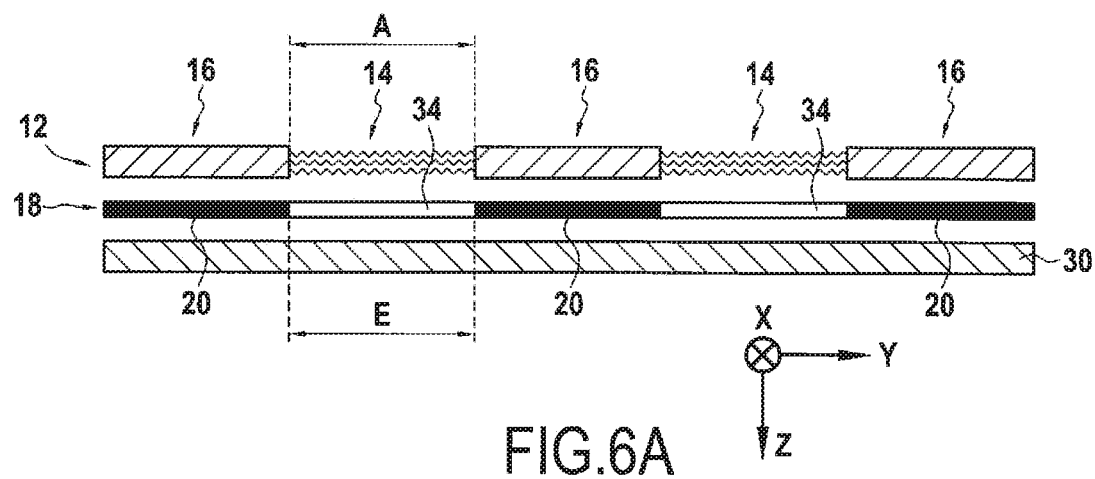
FIG. 6A is exploded cross-section diagrammatic exploded view of a laminated assembly according to a sixth embodiment.

In the sixth embodiment shown in FIG. 6A, the laminated assembly 10 includes a first non-woven sheet 12 similar to the non-woven sheet of FIG. 1A and a second non-woven sheet similar to the second non-woven sheet of FIG. 3A.

In the sixth embodiment, the adhesive 18 is coated directly on the first non-woven sheet 12. This adhesive includes solid strips 20 of adhesive and solid strips 34 of elastic adhesive. The solid strips 34 of elastic adhesive form the elastic films. The second non-woven sheet 30 is then applied against the first non-woven sheet coated in the adhesive comprising the solid strips 34 of elastic adhesive, the adhesive 18, and thus the solid strips 34 of elastic adhesive, being interposed between the non-woven sheets 12, 30.

In the sixth embodiment, the width A of the activated zone 14 is equal to the width E of the solid strips 34 of the elastic adhesive. It is possible to envisage the width A is greater than or less than the width E.

As in the above embodiments, it is also possible to have some other number of elastic films 24 and/or of activated zones 14. The second non-woven sheet 30 could include one or more activated zones 14.

It is also possible to envisage activating the laminated assembly 10 in the zones of the laminated assembly where the slid strips 34 of elastic adhesive are present. Since the first non-woven sheet 12 was activated prior to laminating the first non-woven sheet 12 with the adhesive 18, the degree of activation of the activated zones 14 of the first non-woven sheet 12 is modified by activating the laminated assembly 10. Nevertheless, the resulting degree of activation of the activated zones 14 of the first non-woven sheet 12 in the lateral direction Y continues to remain different from the degree of activation of the elastic film 24 in the lateral direction Y.

Figure 6B:
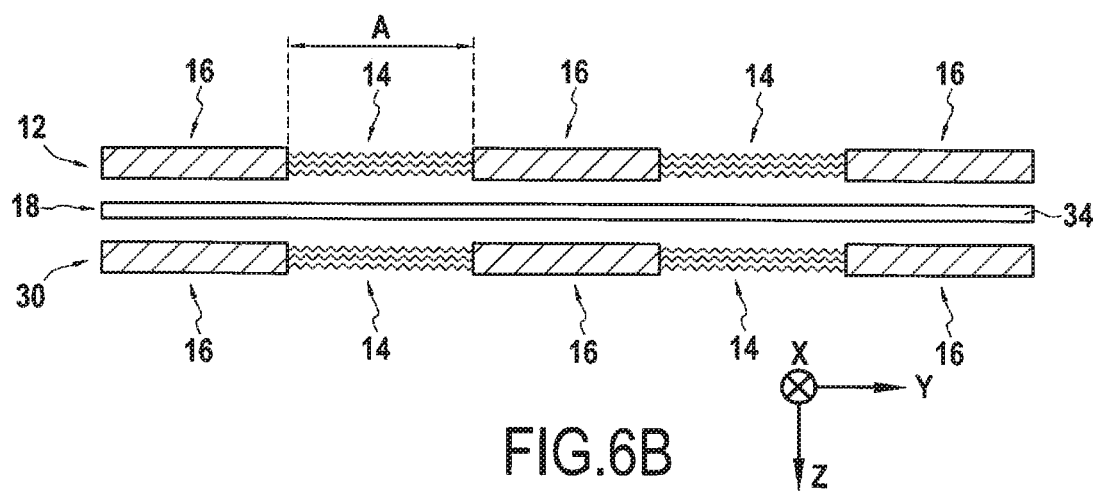
FIG. 6B shows a variant of the sixth embodiment.

In the variant of the sixth embodiment as shown in FIG. 6B, the laminated assembly 10 differs from the laminated assembly of FIG. 6A in that the second non-woven sheet 30 is similar to the non-woven sheet 12 of FIG. 1A and in that the adhesive 18 is constituted by a single solid strip 34 of elastic adhesive. The solid strip 34 of elastic adhesive forms the elastic film.

Figure 7:
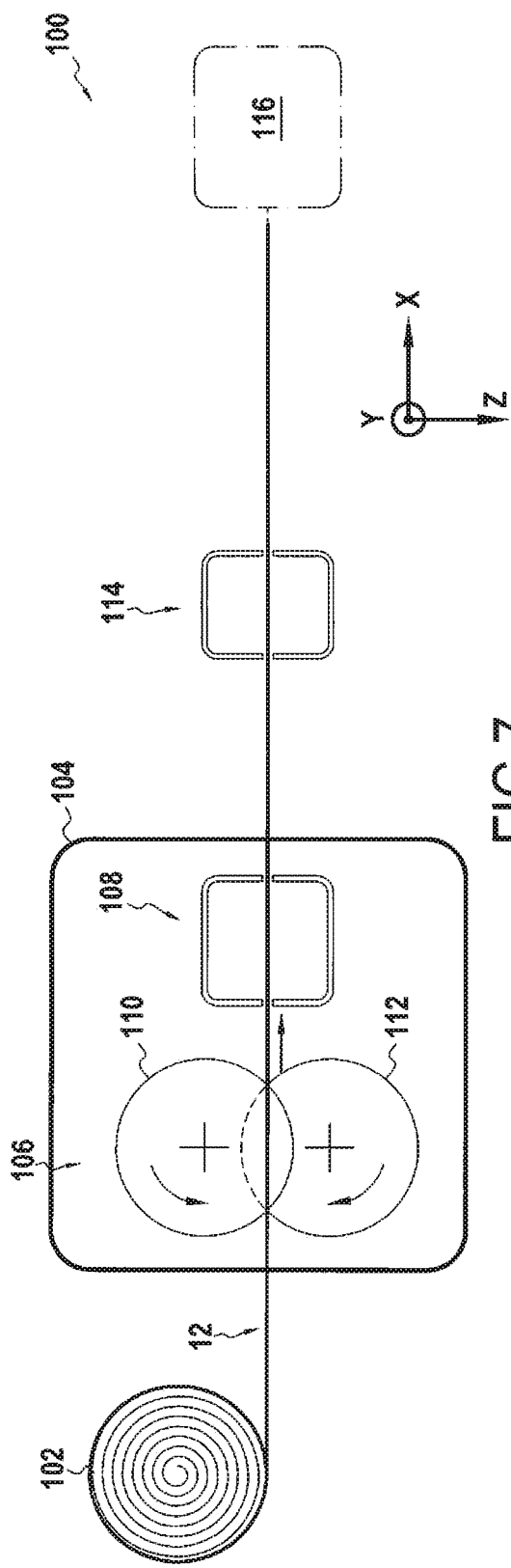
FIG. 7 is a diagrammatic side view of an installation for treating a non-woven sheet.
Figure 8:
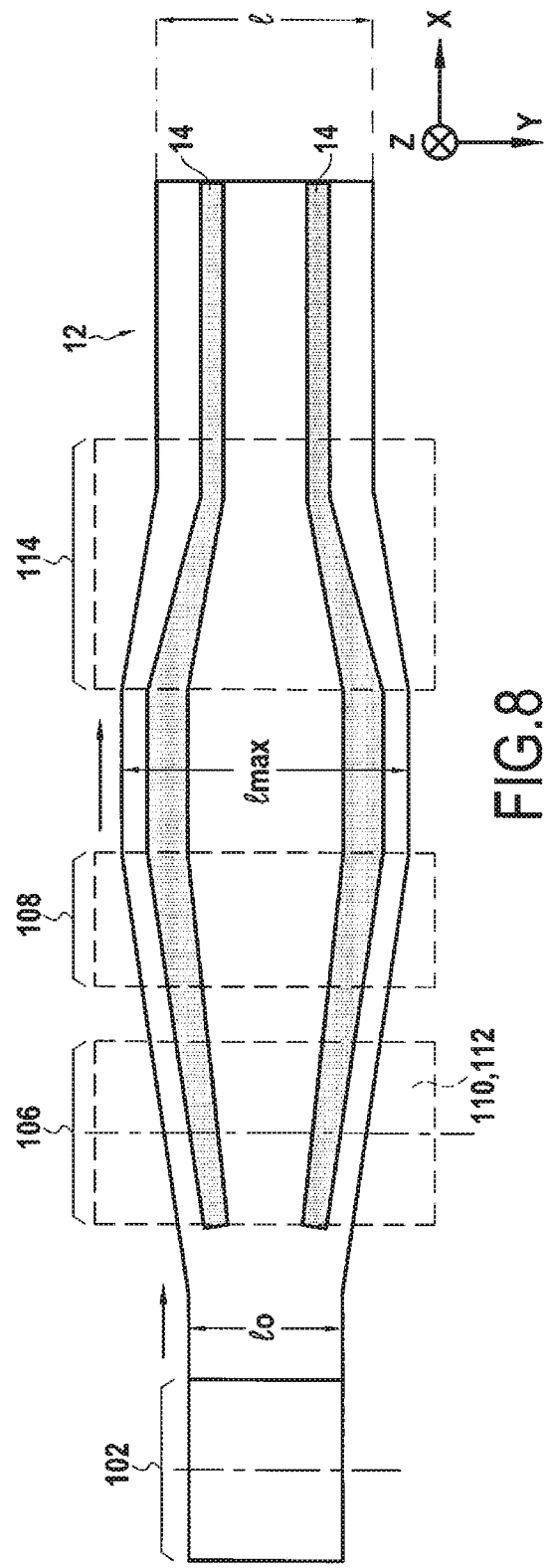
FIG. 8 is a diagrammatic plan view of the non-woven sheet passing at an instant t through the FIG. 7 treatment installation.

FIG. 7 shows a treatment installation 100 for treating a non-woven sheet 12, for making a non-woven sheet 12 and suitable for use in particular upstream from a production line for producing a laminated assembly 10, and FIG. 8 is a diagrammatic plan view of the non-woven sheet 12 passing at an instant t through the treatment installation 100 of FIG. 7, and in which the dimensions of the non-woven sheet 12 are shown diagrammatically.

From upstream to downstream in the travel direction of the non-woven sheet 12 that is to be treated (from left to right in FIG. 7), the installation 100 comprises:
- an unwinding station 102 for unwinding the non-woven sheet 12 that was initially packaged in the form of a reel;
- a widening module 104 for widening the non-woven sheet and comprising:
  - an activation module 106 for activating localized zones of the non-woven sheet 12, forming the activated zones 14 of the non-woven sheet 12; and
  - a stretch module 108 for stretching the non-woven sheet 12 in its lateral direction Y; and
- a width management module 114 for managing the sheet width of the non-woven sheet 12.

Once unwound, the non-woven sheet 12 is activated locally by the activation module 106 (step 200).

Figure 9:
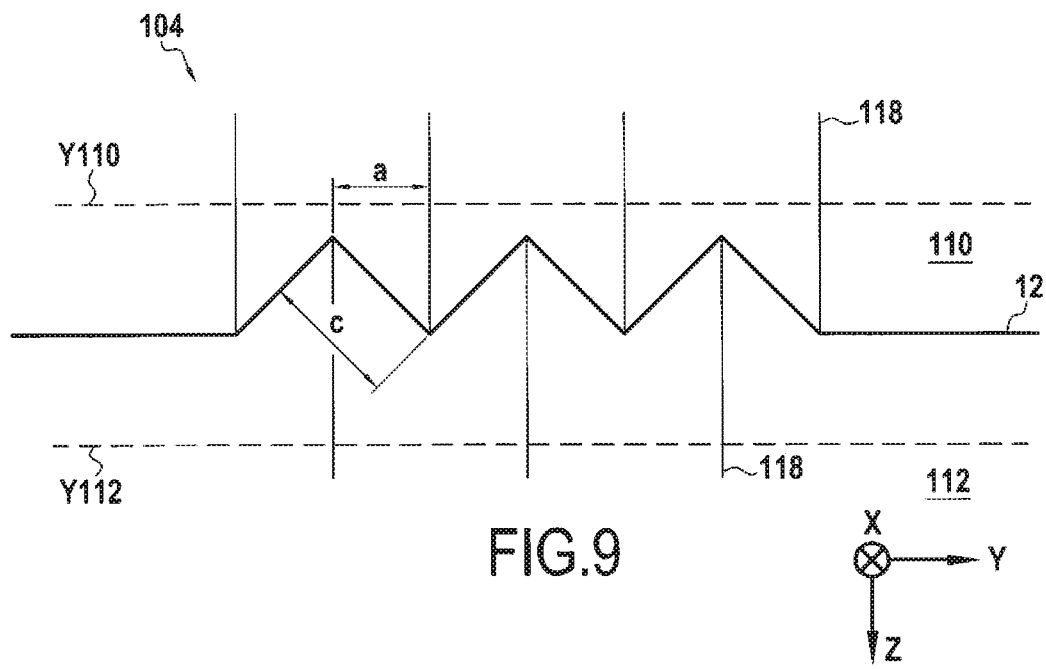
FIG. 9 is a diagrammatic view of the FIG. 7 activation module.

FIG. 9 is a diagrammatic section view on plane YZ of the activation module 106. The activation module 106 includes two activation rollers 110, 112 each provided with a stack of parallel disks 118 that are spaced apart from one another by a distance 2a. The activation rollers 110, 112 and the disks 118 present respective axes of symmetry Y110, Y112 extending in the lateral direction Y. The disks 118 of the first activation roller 110 are arranged in the gaps between the disks of the second activation roller 112, and the axes of symmetry Y110, Y112 of the two activation rollers 110, 112 are spaced apart from each other by a distance that is less than the diameter of the disks 118, such that the zones of the non-woven sheet 12 that pass between the disks 12 of the activation rollers 110, 112 are stretched in the lateral direction Y, thereby forming the activated zones 14. In these locations, the fibers and/or filaments of the non-woven sheet 12 are stretched and/or broken. It may be understood that the smaller the distance between the axes of symmetry Y110, Y112 of the two activation rollers 110, 112, the greater the interpenetration of the disks 118 of the first activation roller 110 relative to the second activation roller 112, and thus the greater the degree of activation.

In known manner, the degree of activation is expressed as a percentage and is the ratio of the difference between the distance c between the ends of two adjacent disks each belonging to a different activation roller minus the distance between the ends of the same two disks as projected onto the axis of symmetry of an activation roller divided by this distance a between the ends of the same two disks as projected onto the axis of symmetry of an activation roller.

As a percentage, the degree of activation may be expressed as follows:

$$\text{degree of activation} = [(c-a)/a] \times 100$$

The non-woven sheet 12 is then deformed more generally by the stretch module 108 that generally comprises a plurality of rollers (not shown) for the purpose of stretching the non-woven sheet laterally. It is stretched therein until it occupies a maximum working width lmax greater than the working width l desired for the laminated assembly that is fabricated downstream from the production line 116.

In the width management module 114, which comprises means for measuring the width of the non-woven sheet 12 and means for adjusting this width to a desired value, e.g. by stretching it, the width of the non-woven sheet 12 is adjusted to the working width l that it is to conserve throughout the production line 116.

EXAMPLES

A plurality of laminated assemblies 10 were made.

Examples 1 and 2: the laminated assembly 10 included two non-woven sheets, a first non-woven sheet of carded and calendared type, including two zones 14 that were previously activated to a degree of activation of 153%, and a second non-woven sheet of Spunlace type including zones 14 that were previously activated to a degree of activation of 44%.

Example 3: the laminated assembly 10 included two non-woven sheets, a first non-woven sheet of carded and calendared type, including zones 14 that were previously activated to a degree of activation of 106% and a second non-woven sheet of Spunlace type including zones 14 previously activated to a degree of activation of 44%.

Example 4: the laminated assembly 10 included two non-woven sheets, a first non-woven sheet of carded and calendared type, including zones 14 that were previously activated to a degree of activation of 153%, and a second non-woven sheet of Spunlace type having no previously activated zone.

Example 5: the laminated assembly 10 included two non-woven sheets, a first non-woven sheet of carded and calendared type, having zones 14 previously activated to a degree of activation of 106%, and a second non-woven sheet of Spunlace type having no previously activated zone.

Example 6: the laminated assembly 10 included two non-woven sheets, a first non-woven sheet of carded and calendared type, including zones 14 previously activated to a degree of activation of 153%, and a second non-woven sheet of Spunlace type having no previously activated zone, and the laminated assembly 10 was subsequently activated to a degree of activation of 88%.

Two control examples were also made in which no non-woven sheet was activated prior to laminating. These Examples 7 and 8 each included two non-woven sheets, a first non-woven sheet of carded and calendared type, having no activated zone, and a second non-woven sheet of Spunlace type having no activated zone, and the laminated assembly was subsequently activated to respective degrees of activation of 110% and 93%.

All of the Examples were fabricated at travel speeds on the production line 116 greater than 200 meters per minute (m/min) with the exception of Examples 2 and 3 which were fabricated at travel speeds on the production line 116 of less than 200 m/min.

Thereafter, the elongation at 10 N expressed in millimeters was measured on Examples 1-8, the measurement samples having a width of 50 mm, stretching being performed in the lateral direction Y on a width of 30 mm at a speed of 100 mm/min. The width of 30 mm was selected so only one activated zone was tested. The value of the maximum force (in N) prior to breakage was also measured for each of the samples. The results are summarized in Table 1 below.

TABLE 1

| Example | Elongation for 10 N (in mm) | Maximum force (in N) |
| --- | --- | --- |
| Example 1 | 25.0 | 38 |
| Example 2 | 25.1 | 38 |
| Example 3 | 20.2 | 40 |
| Example 4 | 21.2 | 41 |
| Example 5 | 19.7 | 42 |
| Example 6 | 27.7 | 37 |
| Example 7 | 28.0 | 35 |
| Example 8 | 24.5 | 37 |

It may be seen that by activating at least one non-woven sheet prior to laminating, laminated assemblies 10 are obtained (Examples 1-6) that present elongation at 10 N that are similar for Examples 1 to 5 to the values obtained for Examples 7 and 8 without activating the laminated assembly 10. It may also be seen that the maximum force that the laminated assemblies 10 may withstand before breaking (Examples 1 to 6) is greater than the maximum force that may be withstood by the laminated assemblies of Examples 7 and 8. The laminated assemblies 10 of Examples 1 to 6 may therefore be subjected to traction forces in the lateral direction Y that are greater than the traction forces to which the laminated assemblies of Examples 7 and 8 may be subjected in the lateral direction Y.

Furthermore, it should be observed that the travel speed on the production line 116 for the non-woven sheets does not influence the properties of the laminated assembly 10 (see in particular Examples 1 and 2). Thus, although previously activated non-woven sheets were used, there was no need to reduce the travel speed on the production line. Furthermore, it was observed that the laminated assembly of Example 4 presents a texture and/or appearance that is more uniform than the texture and/or appearance of the laminated assembly of Example 8. The laminated assembly of Example 8 presents a texture and/or appearance that is more uniform than the texture and/or appearance of the laminated assembly of Example 6. A texture and/or appearance is said to be "more uniform" when the laminated assembly has fewer zones of differing contrast once the laminated assembly has been stretched. For example, for a stretching value obtained under a force of 10 N in the cross-direction (CD), i.e. in the lateral direction Y, for a sample having a CD dimension lying in the range 35 mm to 50 mm, and a machine direction (MD) dimension, i.e. in the longitudinal direction X, lying in the range 50 mm to 100 mm.

Elongation measurements at 5 N were also made on the non-woven sheets on their own prior to lamination. Those elongation measurements at 5 N were performed with a pre-load of 0.1 N, and at a speed of 500 mm/min. The elongation measurements were performed in the lateral direction Y (also "CD"), and in the longitudinal direction X (also "MD").

The results are given in Table 2 below, in which elongation at 5 N is expressed in % of the initial length of the non-woven sheet.

The non-woven fabric 1 was a carded and calendared non-woven fabric previously activated to 153% and weighing 22 grams per square meter ($g/m^2$).

The non-woven fabric 2 was a 22 $g/m^2$ carded and calendared non-woven fabric previously activated to 106%.

The non-woven fabric 3 was a 22 $g/m^2$ carded and calendared non-woven fabric that was not previously activated.

The non-woven fabric 4 was a 30 $g/m^2$ non-woven fabric of Spunlace type, previously activated to 44%.

The non-woven fabric 5 was a 30 $g/m^2$ non-woven fabric of Spunlace type that was not previously activated.

TABLE 2

| Example | Direction | Elongation at 5 N (in %) |
| --- | --- | --- |
| Non-woven fabric 1 | CD | 117 |
| Non-woven fabric 2 | CD | 72 |
| Non-woven fabric 3 | CD | 78 |
| Non-woven fabric 4 | CD | 105 |
| Non-woven fabric 5 | CD | 102 |
| Non-woven fabric 1 | MD | 5.4 |
| Non-woven fabric 2 | MD | 4.1 |
| Non-woven fabric 3 | MD | 2.8 |
| Non-woven fabric 4 | MD | 4.4 |
| Non-woven fabric 5 | MD | 3.0 |

The non-woven fabrics 1 to 5 presented a weight lying in the range 10 grams (g) to 40 g.

It may be seen that the non-woven fabric 1 presents elongation similar to the non-woven fabric 4 or to the non-woven fabric 5, in the CD direction.

Although the present disclosure is described with reference to specific embodiments, it is clear that various modifications and changes may be undertaken on those embodiments without going beyond the general ambit of the invention as defined by the claims. In addition, individual characteristics of the various embodiments mentioned may be combined in additional embodiments. Consequently, the description and the drawings should be considered in a sense that is illustrative rather than restrictive. Thus, it is possible to envisage other pairs for the first and second non-woven sheets 12, 30, e.g.:
- a carded and calendared non-woven fabric and a Spunlace non-woven fabric; or
- a Spunlace non-woven fabric and a Spunlace non-woven fabric; or
- a carded and calendared non-woven fabric and a Spunmelt non-woven fabric; or
- a Spunmelt non-woven fabric and a Spunlace non-woven fabric.

For the above-mentioned examples, the first and second non-woven sheets may be interchanged.

The invention claimed is:

1. A laminated assembly extending in a longitudinal direction and a lateral direction orthogonal to the longitudinal direction, the assembly comprising a non-woven sheet and an elastic film that are laminated together, the non-woven sheet including at least one activated zone extending over the length of the non-woven sheet measured in the longitudinal direction and over a width that is strictly less than the width of the non-woven sheet measured in the lateral direction, the at least one activated zone of the non-woven sheet being activated by being stretched in the lateral direction orthogonal to the longitudinal direction before the non-woven sheet and the elastic film are laminated together such that:

a degree of activation of the at least one activated zone of the non-woven sheet in the lateral direction is different from a degree of activation of the elastic film in the lateral direction, the degree of activation of the at least one activated zone of the non-woven sheet in the lateral direction lying in the range 20% to 200%.

2. The laminated assembly according to claim 1, wherein the non-woven sheet is a first non-woven sheet, the laminated assembly including a second non-woven sheet, and the elastic film being interposed between the first and second non-woven sheets.

3. The laminated assembly according to claim 2, wherein the second non-woven sheet does not include an activated zone.

4. The laminated assembly according to claim 2, wherein the second non-woven sheet includes at least one activated zone extending over the length of the non-woven sheet measured in the longitudinal direction and over a width that is strictly less than the width of the non-woven sheet measured in the lateral direction, a degree of activation of the activated zone of the second non-woven sheet in the lateral direction lying in the range 20% to 200%.

5. The laminated assembly according to claim 2, wherein the degree of activation of the activated zone of the first non-woven sheet in the lateral direction is different from a degree of activation of an activated zone of the second non-woven sheet in the lateral direction.

6. The laminated assembly according to claim 2, wherein a degree of activation of an activated zone of the second non-woven sheet in the lateral direction is different from the degree of activation of the elastic film in the lateral direction.

7. The laminated assembly according to claim 1, wherein the non-woven sheet is a carded and calendared non-woven fabric.

8. The laminated assembly according to claim 1, wherein the non-woven sheet is a non-woven fabric of Spunlace type.

9. The laminated assembly according to claim 1, wherein the non-woven sheet is a non-woven fabric of Spunmelt type.

10. A fabrication method for fabricating a laminated assembly according to claim 1, the laminated assembly extending in the longitudinal direction and in the lateral direction orthogonal to the longitudinal direction, the method comprising the following steps:
  activating in the lateral direction to the degree in the range 20% to 200% a zone of the non-woven sheet extending over the length of the non-woven sheet measured in the longitudinal direction and over the width that is strictly less than the width of the non-woven sheet measured in the lateral direction;
  providing the elastic film; and
  laminating the non-woven sheet with the elastic film after activating the zone of the non-woven sheet.

11. The fabrication method according to claim 10, including, prior to laminating the non-woven sheet, a step of coating the non- woven sheet with an adhesive.

12. The fabrication method according to claim 10, the non-woven sheet being a first non-woven sheet, the fabrication method including a step of providing a second non-woven sheet and a step of laminating the second non-woven sheet on the elastic film.

13. The fabrication method according to claim 12, wherein, prior to laminating the second non-woven sheet, the second non-woven sheet is activated in the lateral direction to a degree lying in the range 20% to 200% over a zone extending over the length of the non-woven sheet measured in the longitudinal direction and over a width that is strictly less than the width of the non-woven sheet measured in the lateral direction.

14. The fabrication method according to claim 13, including, prior to laminating the second non-woven sheet, a step of coating the second non-woven sheet with an adhesive.

15. The fabrication method according to claim 10, wherein the laminated assembly is activated to a degree of less than 200% in the lateral direction.

16. The laminated assembly according to claim 1, wherein the non-woven sheet is a first non-woven sheet, the laminated assembly including a second non-woven sheet, and the second non-woven sheet being interposed at least in part between the first non-woven sheet and the elastic film.

17. The laminated assembly according to claim 16, wherein the second non-woven sheet includes at least one activated zone extending over the length of the non-woven sheet measured in the longitudinal direction and over a width that is strictly less than the width of the non-woven sheet measured in the lateral direction, the degree of activation of the activated zone of the second non-woven sheet in the lateral direction lying in the range 20% to 200%.

18. The laminated assembly according to claim 16, wherein the second non-woven sheet does not include an activated zone.

19. The laminated assembly according to claim 16, wherein the degree of activation of the activated zone of the first non-woven sheet in the lateral direction is different from a degree of activation of an activated zone of the second non-woven sheet in the lateral direction.

20. The laminated assembly according to claim 16, wherein a degree of activation of an activated zone of the second non-woven sheet in the lateral direction is different from the degree of activation of the elastic film in the lateral direction.

21. The fabrication method according to claim 10, the non-woven sheet being a first non-woven sheet, the fabrication method including a step of providing a second non-woven sheet, and a step of laminating the second non-woven sheet with the first non-woven sheet.

22. The fabrication method according to claim 21, wherein, prior to laminating the second non-woven sheet, the second non-woven sheet is activated in the lateral direction to a degree lying in the range 20% to 200% over a zone extending over the length of the non-woven sheet measured in the longitudinal direction and over a width that is strictly less than the width of the non-woven sheet measured in the lateral direction.

23. The fabrication method according to claim 22, including, prior to laminating the second non-woven sheet, a step of coating the second non-woven sheet with an adhesive.

* * * * *